(12) United States Patent
Khamar

(10) Patent No.: US 7,972,609 B2
(45) Date of Patent: Jul. 5, 2011

(54) METHOD OF TREATING CANCER

(75) Inventor: Bakulesh Mafatlal Khamar, Gujarat (IN)

(73) Assignee: Cadila Pharmaceuticals Ltd., Ahmedabad, Gujarat (IN)

( * ) Notice: Subject to any disclaimer, the term of this patent is extended or adjusted under 35 U.S.C. 154(b) by 269 days.

(21) Appl. No.: 10/502,417

(22) PCT Filed: Dec. 10, 2002

(86) PCT No.: PCT/IB02/05516
§ 371 (c)(1),
(2), (4) Date: Feb. 15, 2007

(87) PCT Pub. No.: WO03/049667
PCT Pub. Date: Jun. 19, 2003

(65) Prior Publication Data
US 2007/0259005 A1    Nov. 8, 2007

(30) Foreign Application Priority Data
Dec. 10, 2001   (IN) .......................... 1167MUM/2001

(51) Int. Cl.
*A61K 39/04*   (2006.01)

(52) U.S. Cl. .................................. 424/248.1; 424/234.1
(58) Field of Classification Search ............... 424/234.1, 424/248.1; 435/243, 252.1, 253.1
See application file for complete search history.

(56) References Cited

U.S. PATENT DOCUMENTS

| | | |
|---|---|---|
| 5,767,156 A | 6/1998 | Ferrante et al. |
| 5,869,645 A | 2/1999 | Groves |
| 6,030,618 A | 2/2000 | Srivastava |
| 6,033,669 A | 3/2000 | Jondal |
| 6,056,964 A | 5/2000 | Rook et al. |
| 6,080,725 A | 6/2000 | Marciani |
| 6,090,385 A | 7/2000 | Maes |
| 6,221,351 B1 | 4/2001 | Terman |

*Primary Examiner* — Jennifer Graser
(74) *Attorney, Agent, or Firm* — Burns & Levinson LLP

(57) ABSTRACT

Present invention relates to the method of treating cancer. According to present invention, a pharmaceutical composition made from '*Mycobacterium w*' ($M_w$) is found to be useful in the management of cancer. We have now found that the same therapeutic agent is useful in management of cancer. The use of *Mycobacterium w* containing formulations is associated with decrease in burden of cancer tissue, decreasing symptoms associated with cancer and improving quality of life. It also improves tolerance to other therapies.

29 Claims, 6 Drawing Sheets

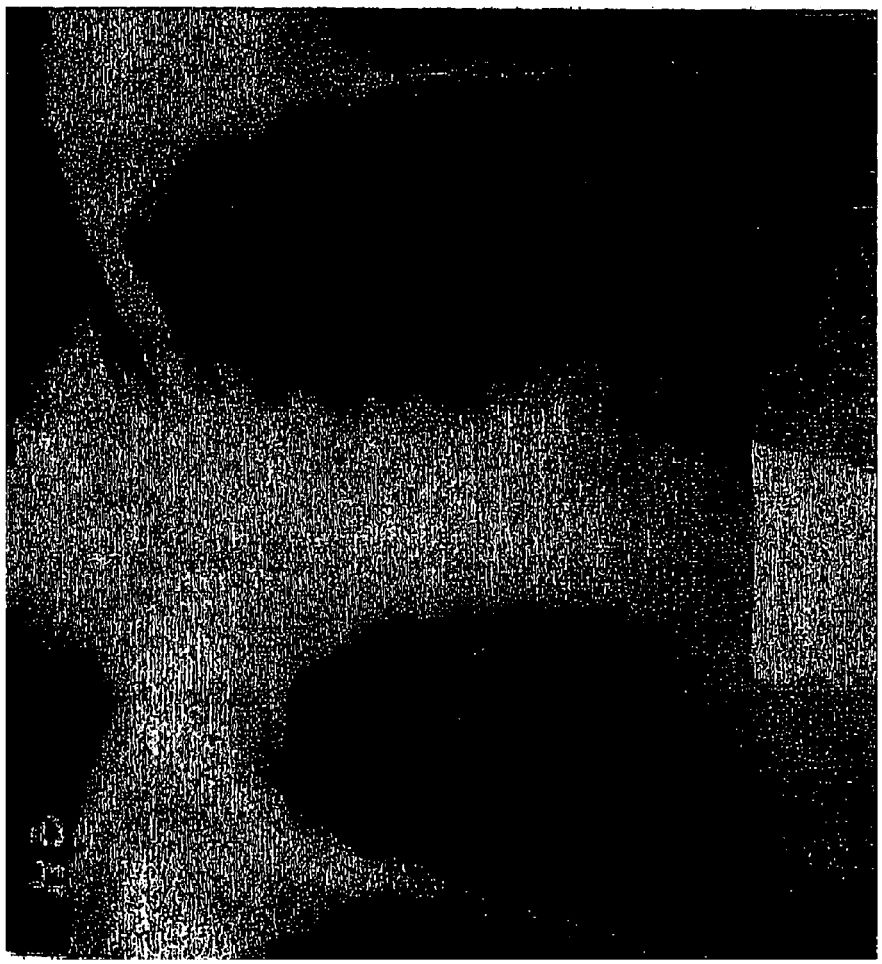
Figure-1 is X ray non small cell lung cancer before treatment – subject 1

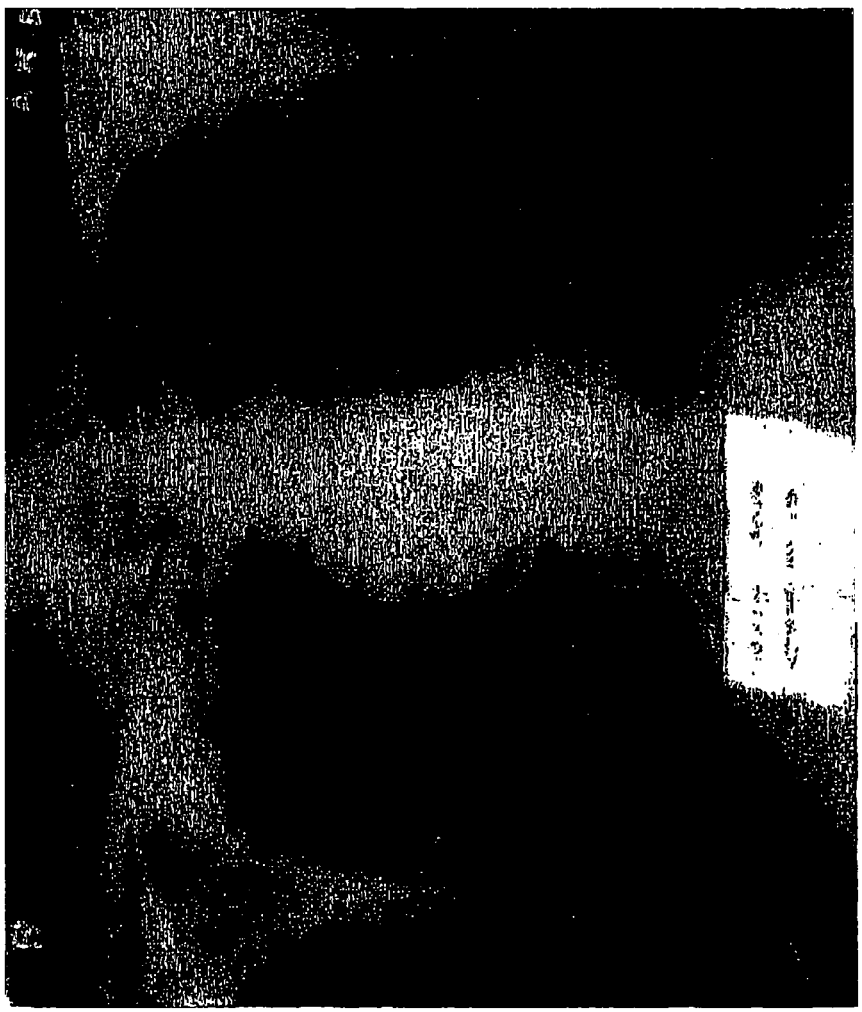
Figure-2 is X ray non small cell lung cancer after treatment –subject 1

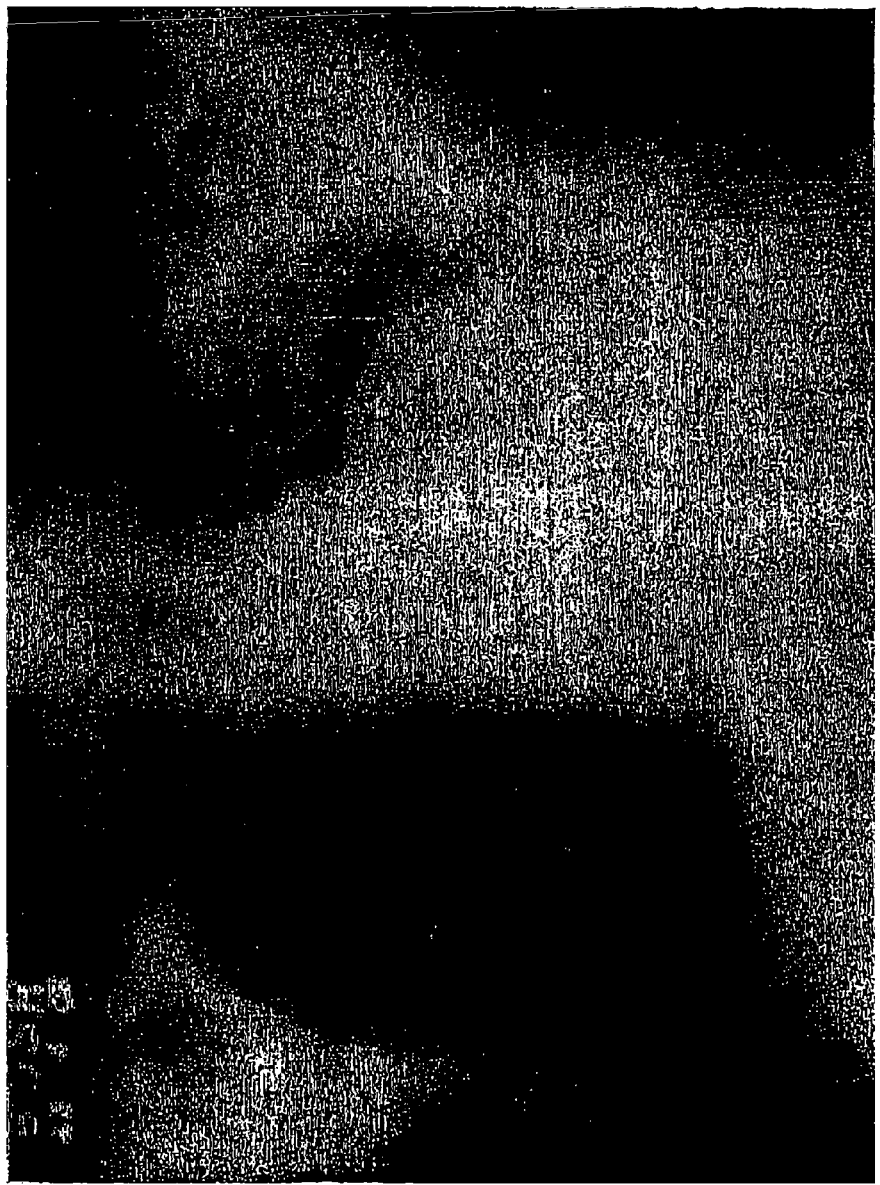
Figure-3 is X ray non small cell lung cancer before treatment – subject 2

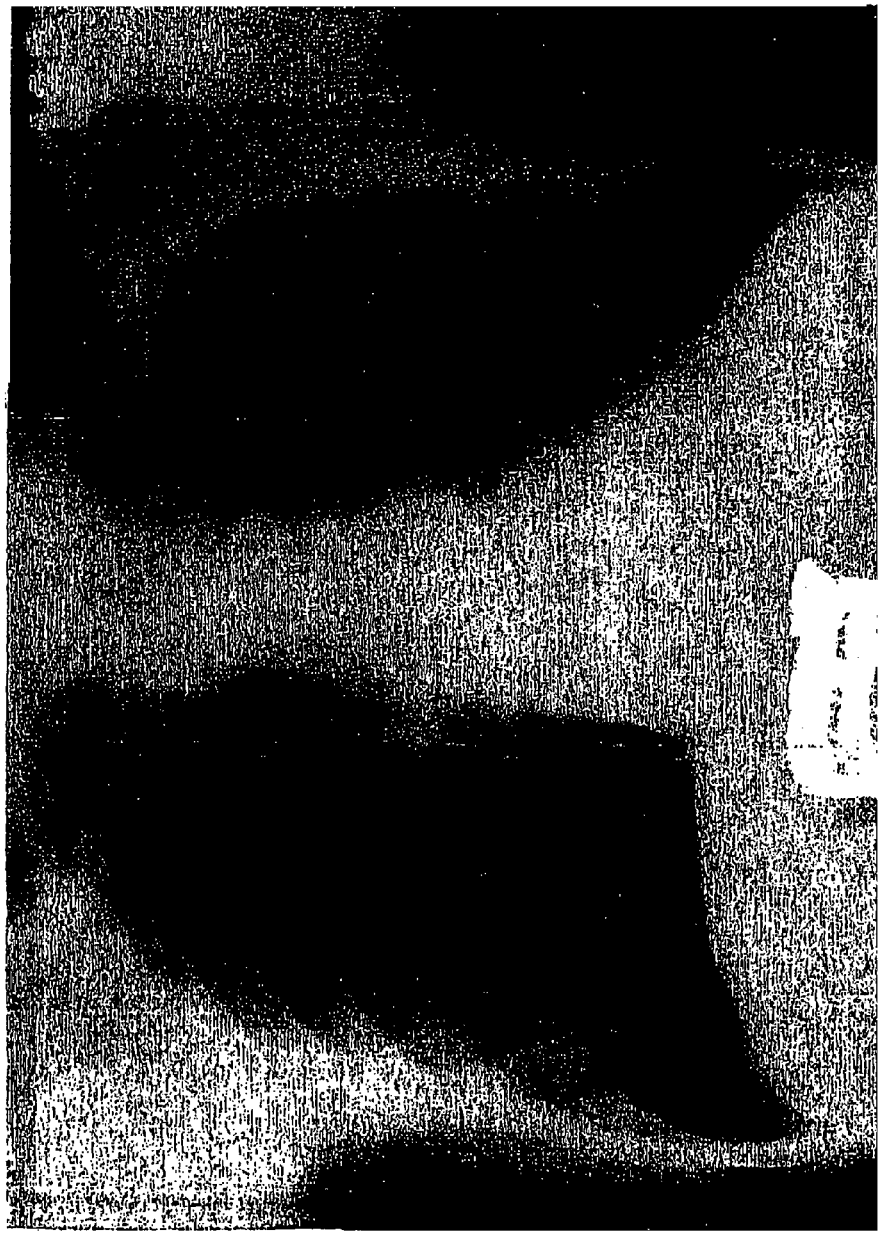
Figure-4 is X ray non small cell lung cancer after treatment-subject 2

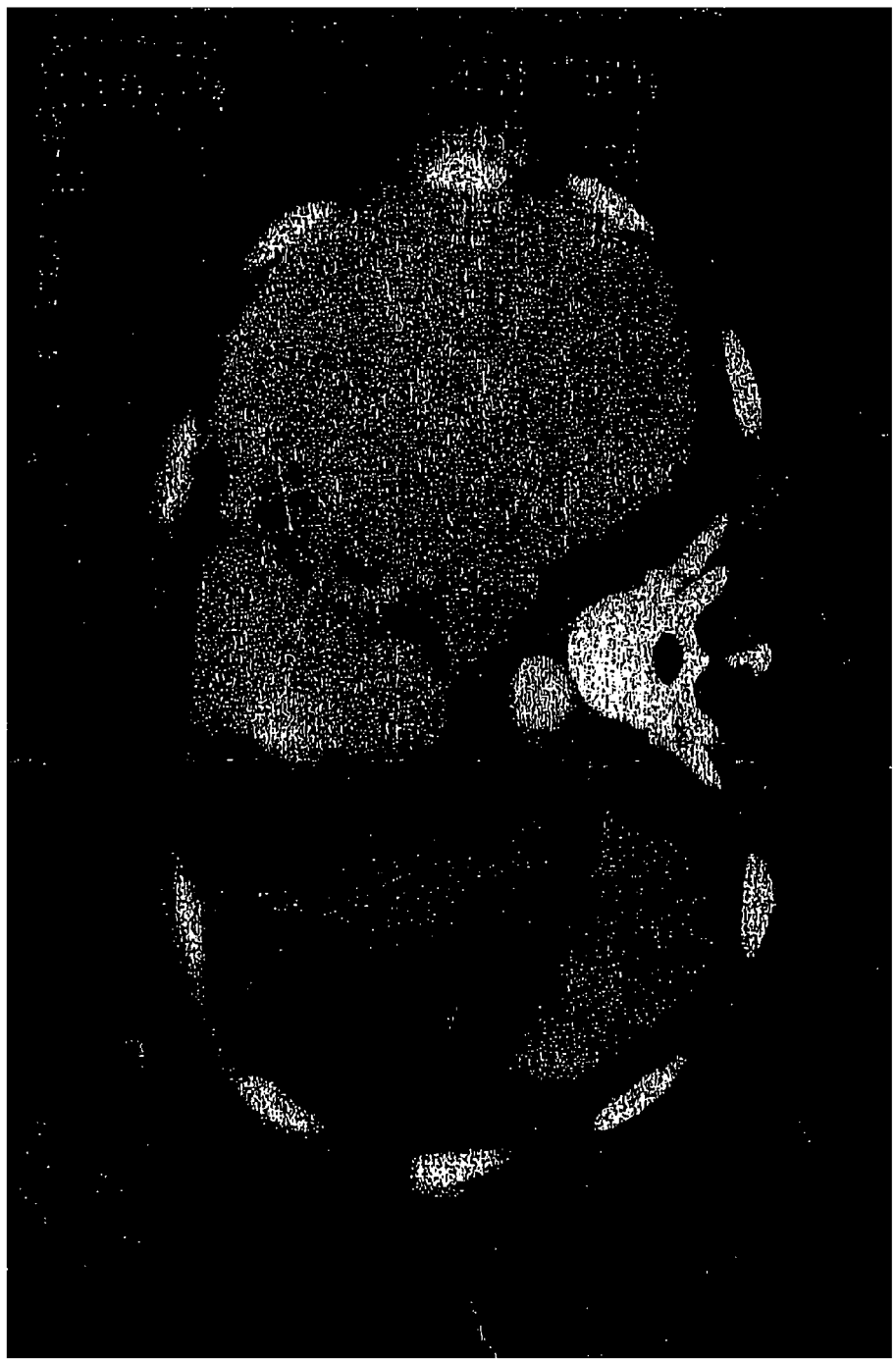
Figure-5 is CT Scan report of patient operated for colorectal cancer with liver metastatisis before treatment (38 x38 mm)

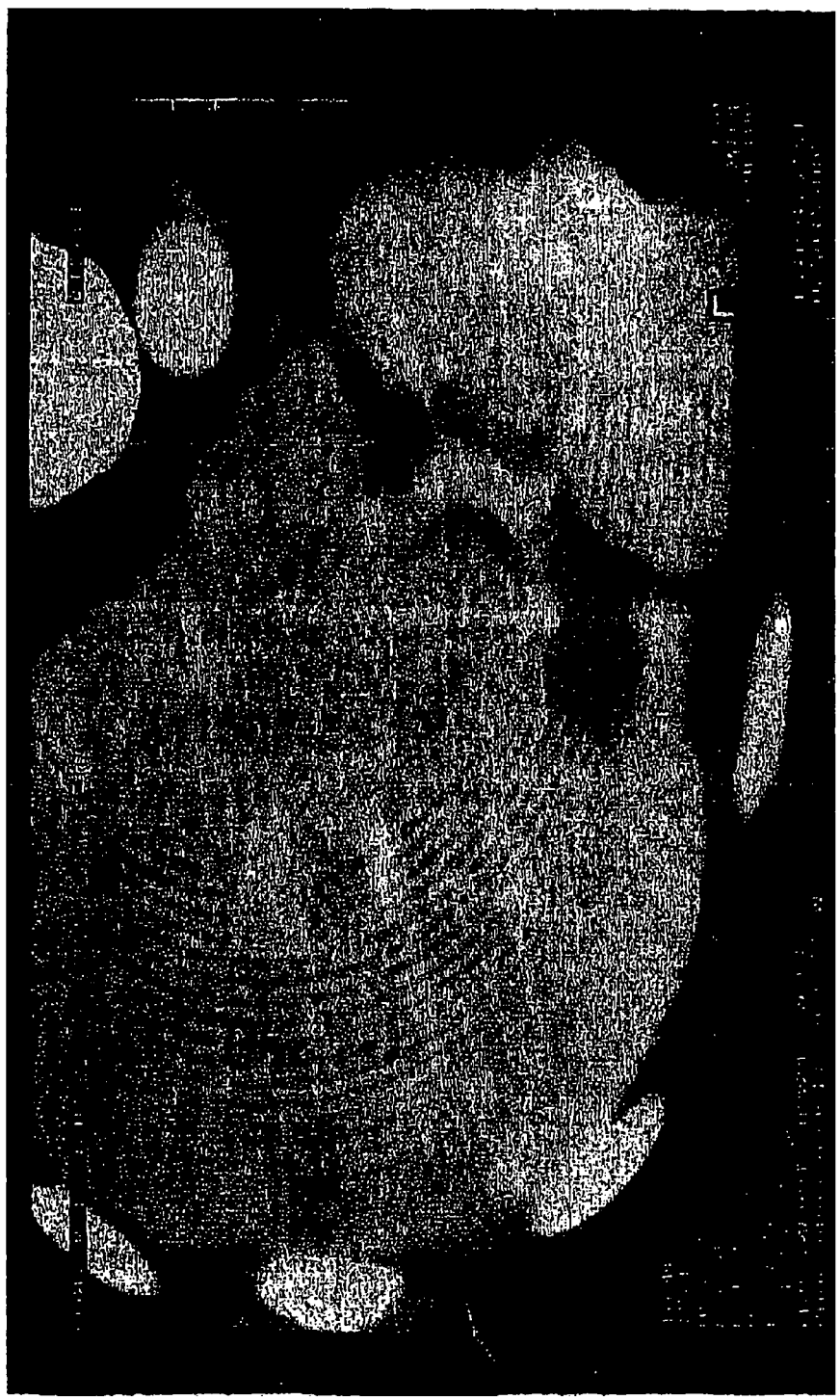
Figure-6 is CT Scan report of patient operated for colorectal cancer with liver metastatisis after treatment (20 x 20 mm)

METHOD OF TREATING CANCER

CROSS REFERENCE TO PRIOR APPLICATIONS

This application is a U.S. National Phase application under 35 U.S.C. §371 of International Application No. PCT/IB02/05516, filed on Feb. 15, 2007 and claims benefit to Indian Patent Application No. 1167MUM/2001, filed on Dec. 10, 2001. The International Application was published in English on Nov. 8, 2007 as WO 2003/049667 under PCT Article 21(2).

BACKGROUND OF THE INVENTION

Cancer is believed to be caused by defective immune system. Many attempts have been made to improve immune system without success. Surprisingly it is found that *Mycobacterium w* containing compositions which are useful in improving immune status in patients with leprosy are also useful in management of cancer. They are found to be useful in decreasing burden of disease and reducing symptoms associated with cancer. More surprising was their synergy with conventional therapy in spite of fact that they work through entirely different mechanism. Still surprising was decrease in side effects of other therapy rather than increase in overall side effects in spite of use in same therapeutic amount along with increase in effect.

PRIOR ART

Treatment of cancer is has traditionally been approached though chemotherapy, coupled with radiotherapy for primary elimination of leukemias, neoplasams and tumors. In contrast surgery has been used to remove solid tumors. Therapy involves both curative and palliative leading to cure and reduction of suffering of the patient. Immunotherapeutic methods have also been found to be effective against a restrictive range of tumors of mesodermal origin suggesting that the immune system is capable of preventing or capable of delaying the growth of tumors in certain cases.

Traditionally BCG vaccine is used for boosting of immunity of individuals with cancer. This has not been well accepted as a mode of therapy due to inconclusive results. The only accepted method of BCG is to use it for bladder cancer by way of intravesicular therapy. The disadvantage associated with use of BCG is development of systemic and local tuberculosis caused by BCG. This is related to the fact that BCG contain live organism and they can be pathogenic to immunocompromised host.

U.S. Pat. No. 6,030,618 discloses an invention related to compositions, methods and kits for the prevention and treatment of primary and metastatic cancers and/or infectious diseases using heat shock/stress proteins (hsp) alone or in combination with each other and antigenic molecules to augment the immune responses to genotoxic and nongenotoxic factors, tumors, pathogens and infectious agents.

U.S. Pat. No. 5,767,156 provides a method of stimulating macrophage neutrophil and/or monocyte function in a subject. The method involves the administration of an effective amount of a free fatty acid having 18-24 carbon chain length with 2-6 double bonds and TNF or a TNF fragment or GMCSF or interferon gamma.

U.S. Pat. No. 6,080,725 is directed to vaccines comprising one or more bacterial, viral, or tumor-associated antigens; and one or more saponin-lipophile conjugate in which the lipophilic moiety such as a lipid, fatty acid, PEG, or terpene is covalently bonded to a non-acylated or deacylated triterpene saponin via a carboxyl group present on the 3-O-glucuronic acid of the triterpene saponin. The bacterial antigen in the vaccine are associated with a bacterial selected from diverse groups of bacteria including *Mycobacterium tuberculosis*.

U.S. Pat. No. 6,221,351 B1 relates generally to tumoricidal compositions and methods and more specifically to superantigens or enterotoxins derived from *Staphlococcus aureus*, peptide homologs to the enterotoxins including shock syndrome toxin, Streptococcal pyrogenic exotoxins, mycoplasma and mycobacterial species, minor lymphocyte stimulating antigens, heat shock proteins, stress \peptides, mammary tumor virus peptides, homologous synthetic polypeptides, biochemically derivatised enterotoxins, genetically engineered enterotoxins and fusion proteins. This invention also relates to superantigens expressed on the surface of lipid droplets in adjuvant-vehicle formulations or expressed in biologic cell surfaces as a result of enterotoxin gene transfection and used to produce a tumorocidal response in tumor bearing hosts. It also relates to enterotoxins and related compounds administered intravenously, subcutaneously, as in adjuvant form, or used extracorporeally in free or bound form to stimulate immunocytes, which are subsequently infused into tumor bearing tissues.

U.S. Pat. No. 6,090,385 discloses a method of treating a cancer patient which comprises administering to said patient an anti-tumor effective amount of at least one of a water-soluble thermostable macromolecular antigen complex which is interspecific of microorganisms of the Mycobacteria, Nocardia, and Corynebacteria group and which exhibits after electrophoresis an immunoelectrophoretic precipitation pattern corresponding to that of the antigen complex 60 of the *Mycobacterium bovis* Calmette Guerin Bacillus strain, or immunogenic fragments of such a complex. It comprises an additional step of administering a therapeutic agent specific against the patient's cancer.

U.S. Pat. No. 6,067,964 suggests the delaying or preventing the growth or spread of breast or bronchial neoplasm which comprises administering to a subject in need of the same, antigenic and/or immunoregulatory material which comprises killed cells of *Mycobacterium vaccae* strain NCTC 11659 in an amount sufficient at least to delay or prevent the growth or spread of said neoplasm. This could be administered by intradermal injection.

U.S. Pat. No. 6,033,669 describes a method of stimulating the generation of cytotoxic T Cells (CTLs) in a patient, wherein the CTLs have the potential to destroy or attenuate cells presenting a characteristic disease-associated carbohydrate structure, which comprises administering to the patient an effective dose of a peptide/carbohydrate conjugate complex capable of generating cytotoxic T cell immunity against a carbohydrate structure, said conjugate structure comprising (i) a peptide component capable of binding an MH class I molecule, and (ii) a carbohydrate component comprising of immunogenic specificity of said disease-associated carbohydrate structure and being of a size that enables a T cell receptor to encompass an epitope of said disease-associated carbohydrate structure. This is claimed to be effective for treatment of melanoma, breast cancer, lung cancer or gastrointestinal cancer.

It has surprisingly been found that pharmaceutical compositions containing *Mycobacterium w* (Mw) are effective in the treatment of a broad range of cancer indications. Pharmaceutical compositions as per present invention may contain extracts of *Mycobacterium w* alone or in combination of *Mycobacterium w*. As per another aspect of present invention pharmaceutical composition may contain other immunomodulator. It can be administered in various ways including intradermal, oral, intralesional etc. The present invention discloses such formulations and the method of their manufacture and use.

*Mycobacterium w* is a rapidly growing *Mycobacterium* which is not a pathogen.

*Mycobacterium w* is a non-pathogenic, cultivable, atypical mycobacterium, with biochemical properties and fast growth characteristics resembling those belonging to Runyons group IV class of Mycobacteria in its metabolic and growth properties but is not identical to those strains currently listed in this group. It is therefore thought that Mw is an entirely new strain. The species identity of Mw has been defined by polymerase chain reaction DNA sequence determination.

It has been found to share antigens with *Mycobacterium leprae* and *Mycobacterium tuberculosis*. It is found to provide prophylaxis against leprosy in humans by converting lepromin negative individuals to lepromin positivity. It is also found to provide prophylaxis against tuberculosis in animals. In leprosy it is also found to reduce duration of therapy for bacterial killing, clearance as well as clinical cure when used along with multi drug therapy.

SUMMARY OF THE INVENTION

According to present invention, a pharmaceutical composition made from *Mycobacterium w* (Mw) is found to be useful in the management of cancer. We have now found that the same therapeutic agent is useful in management of cancer. The use of *Mycobacterium w* containing formulations is associated with decrease in burden of cancer tissue, decreasing symptoms associated with cancer and improving quality of life. It also improves tolerance to other therapies.

Therapeutic agent which may be used in the present invention resembles Mw and non-pathogenic, cultivable, atypical *mycobacterium*, with biochemical properties and fast growth characteristics resembling those belonging to Runyons group IV class of Mycobacteria in its metabolic and growth properties but is not identical to those strains currently listed in this group. It is therefore thought that Mw is an entirely new strain.

The species identity of Mw has been defined by polymerase chain reaction DNA sequence determination and differentiated from thirty other species of mycobacteria. It however differs from those presently listed in this group in one respect or the other. By base sequence analysis of a polymorphic region of pattern analysis, it has been established that $M_w$ Mw is a unique species distinct from many other known mycobacterial species examined which are: *M. avium, M. intracellulare, M. scofulaceum, M. kansasil, M. gastri, M. gordonae, M. shimoidel, M. Malmoense, M. haemorphilum, M. terrae, M. nonchromogenicum, M. trivale, M. marinum, M. flavescens, M. simian, M. szulgal, M. xenopi, M. asciaticum, M. aurum, M. amegrnatis, M. vaccae, M. fortultum* subsp *fortuitum, M. fortuitum* subsp. *Peregrinum, M. chelonae* subsp. *Chelonae, M. chelonae* subsp. *Abscessus, M. genavense, M. tuberculosis, M. tuberculosis* $H_{37}R_v$, *M. paratuberculosis*.

The object of the present invention is to provide a pharmaceutical composition containing *Mycobacterium w* (Mw) for the treatment of cancer.

Another object of the present invention is to provide a pharmaceutical composition containing *Mycobacterium w* (Mw) to improve quality of life in patient suffering from cancer.

Yet another object of the invention is to provide a pharmaceutical composition derived from *Mycobacterium w* that are useful for the management of cancer.

Yet another object of the invention is to provide a pharmaceutical composition derived from *Mycobacterium w* to provide symptomatic relief for patients suffering from cancer.

Yet another object of present invention is to provide a pharmaceutical composition which decreases side effects of standard therapy like radiotherapy, chemotherapy.

Yet another object of present invention is to provide an a pharmaceutical composition containing *Mycobacterium w* (Mw) which decreases burden of cancer cells/tissues of primary and/or secondary (metastatic), sensitive and/or refractory to conventional treatment.

Yet another object of present invention is to provide a pharmaceutical composition which improves effect of conventional therapies.

BRIEF DESCRIPTION IF THE DRAWINGS

FIG. 1 is Xray non small cell lung cancer before treatment—subject 1

FIG. 2 is Xray non small cell lung cancer after treatment—subject 1

FIG. 3 is Xray non small cell lung cancer before treatment—subject 2

FIG. 4 is Xray non small cell lung cancer after treatment—subject 2

FIG. 5 is CT Scan report of patient operated for colorectal cancer with liver metastatisis before treatment FIG. 6 is CT Scan report of patient operated for colorectal cancer with liver metastasis after treatment

DETAILED DESCRIPTION OF THE INVENTION

In accordance with the invention the composition of a pharmaceutical composition the method of preparation, HPLC characteristic its safety and tolerability, methods of use and outcome of treatments are described in following examples. The following are illustrative examples of the present invention and scope of the present invention should not be limited by them.

Example 1

The pharmaceutical compositions:

| A. Each dose of 0.1 ml of therapeutic agent contains: | |
|---|---|
| Mycobacterium w., (heat killed) | $0.50 \times 10^9$ |
| Sodium Chloride I.P. | 0.90% w/v |
| Tween 80 | 0.1% w/v |
| Thiomerosal I.P. (As a Preservative) | 0.01% w/v |
| Water for injection I.P. | q.s. to 0.1 ml |
| B. Each dose of 0.1 ml of therapeutic agent contains: | |
| Mycobacterium w., (heat killed) | $0.50 \times 10^9$ |
| Sodium Chloride I.P. | 0.90% w/v |
| Triton x 100 | 0.1% w/v |
| Thiomerosal I.P. (As a Preservative) | 0.01% w/v |
| Water for injection I.P. | q.s. to 0.1 ml |
| C. Each dose of 0.1 ml of therapeutic agent contains: | |
| Mycobacterium w., (heat killed) | $0.50 \times 10^8$ |
| Sodium Chloride I.P. | 0.90% w/v |
| Thiomerosal I.P. (As a Preservative) | 0.01% w/v |
| Water for injection I.P. | q.s. to 0.1 ml |

-continued

| D. Each dose of 0.1 ml of therapeutic agent contains | |
|---|---|
| Extract of Mycobacterium w after sonication from $1 \times 10^{10}$ Mycobacterium w | |
| Sodium Chloride I.P. | 0.99% w/v |
| Thiomerosal I.P. (As a Preservative) | 0.01% w/v |
| Water for injection I.P. | q.s. to 0.1 ml |
| E. Each dose of 0.1 ml of therapeutic agent contains | |
| Methanol Extract of $1 \times 10^{10}$ Mycobacterium w | |
| Sodium Chloride I.P. | 0.90% w/v |
| Thiomerosal I.P. (As a Preservative) | 0.01% w/v |
| Water for injection I.P. | q.s. to 0.1 ml |
| F. Each dose of 0.1 ml of therapeutic agent contains | |
| Chloroform Extract of $1 \times 10^{10}$ Mycobacterium w | |
| Sodium Chloride I.P. | 0.90% w/v |
| Thiomerosal I.P. (As a Preservative) | 0.01% w/v |
| Water for injection I.P. | q.s. to 0.1 ml |
| G. Each dose of 0.1 ml of therapeutic agent contains | |
| Acetone Extract of $1 \times 10^{10}$ Mycobacterium w | |
| Sodium Chloride I.P. | 0.90% w/v |
| Thiomerosal I.P. (As a Preservative) | 0.01% w/v |
| Water for injection I.P. | q.s. to 0.1 ml |
| H. Each dose of 0.1 ml of therapeutic agent contains | |
| Ethanol Extract of $1 \times 10^{10}$ Mycobacterium w | |
| Sodium Chloride I.P. | 0.90% w/v |
| Thiomerosal I.P. (As a Preservative) | 0.01% w/v |
| Water for injection I.P. | q.s. to 0.1 ml |
| I. Each dose of 0.1 ml of therapeutic agent contains | |
| Liticase Extract of $1 \times 10^{10}$ Mycobacterium w | |
| Sodium Chloride I.P. | 0.90% w/v |
| Thiomerosal I.P. (As a prreservative) | 0.01% w/v |
| Water for injection I.P. | q.s. to 0.1 ml |
| J. Each dose of 0.1 ml of therapeutic agent contains | |
| Mycobacterium w (heat killed) | $0.5 \times 10^7$ |
| Extract of mycobacterium w obtained $1 \times 10^3$ Mycobacterium w by disruption, solvent extraction or enzymatic extraction. | |
| Sodium Chloride I.P. | 0.90% w/v |
| Thiomerosal I.P. (As a Preservative) | 0.01% w/v |
| Water for injection I.P. | q.s. to 0.1 ml |

Example 2

The Process of Preparing a Pharmaceutical Composition

A. Culturing of *Mycobacterium w*.

i) Preparation of culture medium. *Mycobacterium w* is cultured on solid medium like L J medium or liquid medium like middle brook medium or sauton's liquid medium. For better yield middle brook medium is enriched. It can be preferably enriched by addition of glucose, bactotryptone, and BSA. They are used in ratio of 20:30:2 preferably.

The enrichment medium is added to middle brook medium. It is done preferably in ratio of 15:1 to 25:1 more preferably in ratio of 20:1.

ii) Bioreactor Operation a) Preparation of Vessel

The inner contact parts of the vessel (Joints, mechanical seals, o-ring/gasket grooves, etc.) should be properly cleaned to avoid any contamination. Fill up the vessel with 0.1 N NaOH and leave as such for 24 H to remove pyrogenic materials and other contaminants. The vessel is then cleaned first with acidified water, then with ordinary water. Finally, the vessel is rinsed with distilled water (3 times) before preparing medium.

b) Sterilization of Bioreactor

The bioreactor containing 9 L distilled water is sterilized with live steam (indirect). Similarly the bioreactor is sterilized once more with Middlebrook medium. The other addition bottles, inlet/outlet air filters etc. are autoclaved (twice) at 121° C. for 15 minutes. Before use, these are dried at 50° C. oven.

c) Environmental Parameter i. Temperature: 37±0.5.degree. C.

ii. pH: 6.7 to 6.8 initially.

B. Harvesting and Concentrating

It is typically done at the end of $6^{th}$ day after culturing under aseptic condition. The concentration of cells (pelletization) is done by centrifugation.

C. Washing of Cells

The pellet so obtained is washed minimum three times with normal saline. It can be washed with any other fluid which is preferably isotonic.

D. Adding Pharmaceutically Acceptable Carrier

Pyrogen free normal saline is added to pellet. Any other pyrogen free isotonic fluid can be used as a pharmaceutical carrier. The carrier is added in amount so as get to desired concentration of active in final form.

E. Adding Preservative

To keep the product free from other contaminating bacteria for its self life preservative is added. Preferred preservative is thiomesol which is used in final concentration of 0.01% w/v.

F. Terminal Sterilization

Terminal sterilization can be done by various physical methods like application of heat or ionizing radiation or sterile filtration.

Heat can be in the form of dry heat or moist heat. It can also be in the form of boiling or pasturization.

Ionizing radiation can be ultraviolet or gamma rays or microwave or any other form of ionizing radiation.

It is preferable to autoclave the final product.

This can be done before after filling in a final package.

G. Quality Control i. The material is evaluated for purity, sterility.

ii. The organisms are checked for acid fastness after gram staining.

iii. Inactivation test: This is done by culturing the product on L J medium to find out any living organism.

iv. Pathogenicity and/or contamination with pathogen.

The cultured organisms are infected to Balb/c mice. None of the mice should die and all should remain healthy and gain weight. There should not be any macroscopic or microscopic lesions seen in liver, lung spleen or any other organs when animals are killed up to 8 weeks following treatment.

v. Biochemical Test:

The organism is subjected to following biochemical tests:

a) Urease

Tween 80 hydrolysis

Niacin Test

Nitrate Reduction Test

The organism gives negative results in urease, Tween 80 hydrolysis and niacin test. It is positive by nitrate reduction test H. Preparation of Constituents of *Mycobacterium w*.

The constituents of *Mycobacterium w* can be prepared for the purpose of invention by:
Cell Disruption
II. Solvent Extraction
III. Enzymatic Extraction The cell disruption can be done by way of sonication or use of high pressure fractionometer or by application of osmotic pressure ingredient.

The solvent extraction can be done by any organic solvent like chloroform, ethanol, methanol, acetone, phenol, isopropyl alcohol, acetic acid, urea, hexane etc.

The enzymatic extraction can be done by enzymes which can digest cell wall/membranes. They are typically proteolytic in nature. Enzyme liticase and pronase are the preferred enzymes. For the purpose of invention cell constituents of *Mycobacterium w* can be used alone in place of *Mycobacterium w* organisms or it can be added to the product containing *Mycobacterium w*.

Addition cell constituents results in improved efficacy of the product.

Example 3

Characteristics of Constituents of *Mycobacterium w* by HPLC Analysis

The constituents of *Mycobacterium w* used for the purpose of invention when subjected to HPLC analysis gives a single peak at 11 minutes. No other significant peaks are found beyond. The peak is homogenous and devoid of any notch suggesting homogeneity of material obtained HPLC analysis was done using a waters system high performance liquid chromatography apparatus.

| | |
|---|---|
| Column: | Novapak c1860A, 4 μm, 3.9 × 150 mm. |
| The guard column: | Novapak c18 |
| Column Temperature: | 30° C. |
| Flow rate: | 2.5 ml/min |
| Injection volume: | 25 μL. |
| Mobile phase: | |

Solvent A:
HPLC grade methanol.
Solvent B:
HPLC grade methylene chloride

Binary Gradient:

The HPLC gradient initially comprised 98% (v/v) methanol (solvent B). The gradient was increased linearly to 80%. A and 20% B at one minute; 35% A and 65% B at 10 minutes, held for 5 seconds and then decreased over 10 seconds back to 98% A and 2% B.

Example 4

Management of Cancer Refractory to Standard Treatment

CASE 1

A 70 year old female suffering from multiple mycloma was receiving malphalan and prednisolone a therapy for 5 years. The disease recurred with bone pain. Her general condition was poor and she was bedridden. Her hemoglobin was reduced to 5.5 gm. She was put on intradermal injection of a pharmaceutical composition injection of a pharmaceutical composition containing *Mycobacterium w* was per present invention. It was given as 0.1 ml intradermally over deltoid region at the interval of one week. At the end of 3 months she is symptoms general condition has improved drastically and she is able to walk on her own. Her hemoglobin value has risen to 7.7 gm/dl from 5.5 gm/dl in absence of any specific treatment on anaemia.

CASE 2

A 50 year old postmenopausal woman under went lumpectomy for a fumigating mass in her last breast (carcinoma breast $T_4$, $N_1$ $M_1$). The tumor was hormone independent and receptor status for estrogen and progesterone was negative. Following surgery she developed cough and breathlessness. It was found to be due to large metastatic lesion in her chest. A pharmaceutical composition as per present invention was added to her therapy. At the end of the three months, there was a remarkable improvement in her cough and breathlessness. X-ray chest showed 25% decrease in size of metastatic lesion. The *Mycobacterium w* containing pharmaceutical composition as per present invention was administered intradermally over deltoid region.

CASE 3

A 68 year old male suffering from carcinoma esophagusmidthird had received radiotherapy and was on chemotherapy (one cycle completed) He developed dysphagia due to progress of disease. He also had neutropenia with fall in total WBC count. Therapy with a pharmaceutical composition was started. It resulted in improvement in his symptoms gradually. At the end of three months. The swallowing became normal with improvement in general condition and normalization of WBC count. The pharmaceutical composition as per present invention was given as 0.1 ml intradermally at weekly interval $2^{nd}$ dose was delayed and administered at the interval of 15 days instead of 1 week. It comprised of 0.3 ml instead of 0.1 ml.

In case 1 and 3 improvement was seen in spite of absence of chemotherapy while in case 2 chemotherapy (FAC) also continued.

Thus this cases illustrates that pharmaceutical compositions containing *Mycobacterium w* (Mw) as per present invention are useful in treatment of cancer which are refractory to standard therapy. Their useful is associated with amelioration of symptoms, improvement in general well being and quality of life, improvement in other associated conditions like anemia, neutropenia.

Example 5

Effect of Pharmaceutical Composition on Cancer when Used Alone

Superficial bladder cancer presents as hematuria. It is amenable to various forms of therapy. Drugs used to achieve remission are given intravesically e.g. doxorubinocin or BCG.

In four patients with superficial bladder cancer diagnosed cystoscopically pharmaceutical composition as per present invention was given intradermally. It was given as 0.1 ml every month. By six weeks (after two injections) everybody became asymptomatic. Eight weeks later cystoscopy was performed. Surprisingly it was found that there was absence of any detectable lesion cystyoscopically. Six months followup did not reveal any recurrence of symptoms. Cyctoscopy also revealed normal bladder mucosa with absence of detectable lesion.

Thus findings are suggestive of effect of pharmaceutical composition containing *Mycobacterium w* as effective therapy in management of bladder cancer when given intradermally over deltoid region.

Example 6

Effect of *Mycobacterium w* when Radiotherapy is not Adequate

Muscle Invasive Bladder Cancer.

Muscle invasive bladder cancer ($T_4$) can be managed by radical cystectomy. However it is desirable to preserve bladder. Radiotherapy and/or chemotherapy are not adequate in achieving local control/remission of disease.

Five patients with muscle invasive bladder cancer were treated by intradermal injection of *Mycobacterium w* over both deltoid. The intradermal *Mycobacterium w* was repeated every month on any on deltoid for six months. All received standard radiotherapy for a total of 71 gy.

At the end of two months all were symptom free. Cystoscopy and computerized axial tomography (T scan) failed to reveal any detectable lesion suggesting complete remission of disease. All are disease free after a follow-up of 8 months or longer after beginning therapy.

Thus *Mycobacterium w* is effective in achieving complete remission and maintaining it.

No side effects were noticed by any of the patients.

Example 7

Effect of *Mycobacterium w* when Chemotherapy is not Adequate

Non Small Cell Lung Cancer.

Non small cell lung cancer is difficult to manage. It usually does not respond well to chemotherapy, or radiotherapy. The response rate is inversely proportionate to extent of disease. In disease with extent $T_4$ surgery is not indicated and chemotherapy and/or radiotherapy has hardly any effect and carries poor prognosis.

Thus findings of this study suggests that *Mycobacterium w* has significant effect on difficult to treat cancer.

Example 8

Effect of *Mycobacterium w* Containing Therapy on Quality of Life and Side Effects of Chemotherapy a) Carcinoma Breast with Bone Metastasis.

In a controlled study involving 20 patients with a breast cancer and bone metastasis effect of *Mycobacterium w* was evaluated. All patients received chemotherapy in the form of cyclophosphamide, adriamycin and 5-fluorouracil. *Mycobacterium w* containing compositions were given as intradermal injections of 0.1 ml every week for two months followed by every 15 days for two months and monthly for two months for a total duration six months. 10 patients of 20 randomly received it while remaining 10 were kept as controls.

None of the patients in treatment group developed diarrhea and vomiting compared to 8 of 10 patients in control group. Mucositis was seen in 1 patient in treatment group compared to 5 patients in control group. Bone marrow depression as manifested by leucopenia, thrombocytopenia and anemia was seen in 2 patients in treatment group and 6 patients in control group. There was increase in weight in 3 patients in treatment group while none of the patients showed increase in weight. All patients had remarkable improvement in quality of life in treatment group which was not seen in any one in control group.

b) Head and Neck Cancer

In a controlled study in 20 patients with histologically proven advanced head and neck cancer with minimum of 6 months expectancy effect of *Mycobacterium w* was evaluated. Each patient received chemotherapy containing Cisplatin and 5-FU. *Mycobacterium w* was given to randomly selected 10 patients as 0.1 ml intradermally over deltoid region every 15 days for 3 months. The first dose was given as 0.2 ml divided over two deltoid region.

The chemotherapy induced hematological side effects resulted in postponement of chemotherapy in 2 out of 10 patients in treatment group and 5 out of 10 patients in control group.

Mucositis was evident on day 15 after chemotherapy. It was seen in 2 patients in treatment group and 6 patients in control group.

Nausea/vomiting was seen in all patients in control group while in none in treatment group.

Thus use of was useful in reducing side effects of chemotherapy.

Example 9

Use of *Mycobacterium w* in Terminally Sick Patients with Cancer

A 65 year old male patient was diagnosed to have carcinoma pancreas with metastasis in liver and lung. He was judged to be terminally ill with incurable cancer was not offered any treatment. He developed extensive cough and breathlessness and was unable to sleep. He was administered *Mycobacterium w* 0.3 ml intradermally biweekly. Within 10 day his cough was controlled and general condition showed improvement. He started doing all his routine work by himself and started getting normal sleep. If for some reason administration of *Mycobacterium w* was delayed beyond 4 days there used to be recurrence of cough and disturbances in sleep. He lived for 14 weeks after therapy and died natural death. X-ray chest taken before and two months after showed some improvement in lesion. He did not receive any other therapy all throughout.

The *Mycobacterium w* was ameliorating symptoms in terminally ill patient due to cancer.

I claim:

1. A method of treating or managing cancer in a patient in need thereof comprising administering to the patient a pharmaceutical composition comprising an effective amount of heat inactivated *mycobacterium w*, wherein cancer in the patient is a primary cancer or a secondary (metastatic) lesion thereof selected from the group consisting of multiple myeloma, breast cancer, esophageal cancer, bladder cancer, non small cell lung carcinoma, head and neck cancer, pancreatic cancer, a cancer that metastasizes to bone, liver, or lung, or combinations thereof.

2. The method of claim 1, wherein the method provides symptomatic relief from one or more of pain, decreased hemoglobin, cough, breathlessness, dysphagia, neutropenia or irregular sleep in the patient suffering from cancer.

3. The method of claim 1, wherein the method is for increasing efficacy of radiotherapy or chemotherapy in the treatment of cancer.

4. The method of claim 1, wherein the method is for the reducing side effect of the radiotherapy or chemotherapy.

5. The method of claim 4, wherein the side effects are hematological side effects.

6. The method of claim 4, wherein the side effects are reduced to avoid interruption of chemotherapy.

7. The method of claim 4, wherein the side effects are leucopenia, thrombocytopenia, anaemia, nausea, vomiting or mucositis.

8. The method of claim 1, wherein the heat for inactivating is applied by means of autoclaving.

9. The method of claim 1, wherein the pharmaceutical composition further comprises one or more adjuvants.

10. The method of claim 9, wherein the pharmaceutical composition further comprises a surfactant.

11. The method of claim 10, wherein the surfactant is polyoxyethylene (20) sorbitan monooleate.

12. The method of claim 10, wherein the pharmaceutical composition comprises a surfactant in an amount up to 0.4% by weight/volume of the pharmaceutical composition.

13. The method of claim 10, wherein the pharmaceutical composition comprises a surfactant in an amount up to 0.1% by weight/volume of the pharmaceutical composition.

14. The method of claim 1, wherein the *Mycobacterium w* is urease negative, or dose not hydrolyze polyoxyethylene (20) sorbitan monooleate, or does not produce niacin, and provides a strong positive response to nitrate reduction tests.

15. The method of claim 1, wherein the pharmaceutical composition is administered alone or in combination with other modes of therapy selected from radiotherapy and chemotherapy.

16. The method of claim 1, wherein the pharmaceutical composition is administered by parenteral route.

17. The method of claim 1, wherein the pharmaceutical composition is administered by intramuscular, subcutaneous, or intradermal route.

18. The method of claim 1, wherein the effective amount of pharmaceutical composition is in a unit dosage form comprising from about $10^9$ to $10^{10}$ *Mycobacterium w*.

19. The method of claim 1, wherein the pharmaceutical composition further comprises a preservative.

20. A method of improving the quality of life in a patient suffering from cancer comprising administering to the patient a pharmaceutical composition comprising an effective amount of heat inactivated *mycobacterium w*, wherein cancer in the patient is a primary cancer or a secondary (metastatic) lesion thereof selected from one or more of multiple myeloma, breast cancer, esophageal cancer, bladder cancer, non small cell lung carcinoma, head and neck cancer, pancreatic cancer, or a cancer that metastasizes to bone, liver, or lung.

21. The method of claim 20, wherein the improvement in quality of life is obtained in the absence of other modes of treatment.

22. The method of claim 20, wherein the improvement in quality of life is obtained with addition of other modes of treatment selected from radiotherapy and chemotherapy.

23. A method of amelioration of symptoms associated with cancer in a patient in need thereof comprising: administering to the patient with an effective amount of a pharmaceutical composition comprising heat inactivated *mycobacterium w*, wherein the symptoms associated with cancer is selected from the group consisting of pain, decreased hemoglobin, cough, breathlessness, dysphagia, neutropenia and irregular sleep, or combinations thereof.

24. The method of treating cancer according to claims 1, wherein the pharmaceutical composition is administered intradermally.

25. The method of treating cancer according to claims 1, wherein the cancer is superficial bladder cancer and the composition is administered intradermally over the deltoid region.

26. The method of treating cancer according to claims 1, wherein the cancer is muscle invasive bladder cancer and the composition in administered intradermally over the deltoid region.

27. The method of treating cancer according to claim 20, wherein the pharmaceutical composition is administered intradermally.

28. The method of treating cancer according to claim 20, wherein the cancer is superficial bladder cancer and the composition is administered intradermally over the deltoid region.

29. The method of treating cancer according to claim 20, wherein the cancer is muscle invasive bladder cancer and the composition in administered intradermally over the deltoid region.

* * * * *